(12) United States Patent
Holba et al.

(10) Patent No.: US 11,105,786 B2
(45) Date of Patent: Aug. 31, 2021

(54) DETECTION AND QUANTIFICATION OF GAS MIXTURES IN SUBTERRANEAN FORMATIONS

(71) Applicant: ConocoPhillips Company, Houston, TX (US)

(72) Inventors: Albert G. Holba, Houston, TX (US); Dariusz Strapoc, Houston, TX (US); Derik W. Kleibacker, Calgary (CA); Lisa H. Wright, Eagle River, AK (US); Jerry H. Veldhuis, Eagle River, AK (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 0 days.

(21) Appl. No.: 16/234,850

(22) Filed: Dec. 28, 2018

(65) Prior Publication Data

US 2019/0137472 A1     May 9, 2019

Related U.S. Application Data

(63) Continuation-in-part of application No. 13/110,646, filed on May 18, 2011, now abandoned.

(Continued)

(51) Int. Cl.
    *G01N 33/24*        (2006.01)
    *E21B 49/00*        (2006.01)
    (Continued)

(52) U.S. Cl.
    CPC ......... *G01N 33/241* (2013.01); *E21B 49/005* (2013.01); *G01N 33/0027* (2013.01); *G01N 33/2823* (2013.01)

(58) Field of Classification Search
    CPC ... E21B 47/10; E21B 49/005; G01N 33/0027; G01N 33/241; G01N 33/2823
    See application file for complete search history.

(56) References Cited

U.S. PATENT DOCUMENTS

| | | | | |
|---|---|---|---|---|
| 4,941,533 A | * | 7/1990 | Buller | C09K 8/594 |
| | | | | 166/246 |
| 5,168,927 A | * | 12/1992 | Stegemeier | E21B 49/00 |
| | | | | 166/252.6 |

(Continued)

OTHER PUBLICATIONS

Pearson, K. On lines and planes of closest fit to systems of points in space, 1901, Philosophical Magazine 2 (11), pp. 559-572 (Year: 1901).*

(Continued)

*Primary Examiner* — Catherine T. Rastovski
*Assistant Examiner* — Liam R Casey
(74) *Attorney, Agent, or Firm* — Boulware & Valoir

(57) ABSTRACT

Methods and systems are provided for quantifying contributions of gas mixtures in a reservoir compartment by way of isotopic analyses. Differing thermal maturities of the different gas mixtures allow estimation of the relative quantity of each gas mixture present in a total gas mixture. Thermal maturities may be estimated by reference to isotopic analyses of each contributing gas mixture and a commingled gas mixture resulting from commingling each of the individual source gas mixtures. This method may be carried out at various depths to determine relative contributions of each gas mixture to the total gas mixture as a function of wellbore depth. Advantages of certain embodiments include, but are not limited to, higher accuracies and ease of application as compared to conventional methods.

10 Claims, 5 Drawing Sheets

Related U.S. Application Data

(60) Provisional application No. 61/352,168, filed on Jun. 7, 2010.

(51) Int. Cl.
  *G01N 33/00* (2006.01)
  *G01N 33/28* (2006.01)

(56) References Cited

U.S. PATENT DOCUMENTS

| | | | | |
|---|---|---|---|---|
| 5,306,909 | A * | 4/1994 | Jones | G01N 21/3577 |
| | | | | 250/255 |
| 7,124,030 | B2 | 10/2006 | Ellis | |
| 7,174,254 | B2 | 2/2007 | Ellis | |
| 2006/0249288 | A1 | 11/2006 | Drozd | |
| 2007/0169540 | A1 * | 7/2007 | Sterner | E21B 21/01 |
| | | | | 73/19.09 |
| 2008/0135236 | A1 | 6/2008 | Schoell | |
| 2008/0306695 | A1 * | 12/2008 | Fusetti | G01N 33/241 |
| | | | | 702/27 |
| 2010/0161302 | A1 * | 6/2010 | Walters | E21B 43/00 |
| | | | | 703/12 |
| 2010/0212399 | A1 * | 8/2010 | Richards | G01N 30/88 |
| | | | | 73/23.41 |
| 2010/0326651 | A1 * | 12/2010 | Pietrobon | E21B 43/14 |
| | | | | 166/250.01 |
| 2011/0088895 | A1 * | 4/2011 | Pop | E21B 7/04 |
| | | | | 166/254.2 |
| 2011/0091979 | A1 * | 4/2011 | Sharma | G01N 33/18 |
| | | | | 436/56 |
| 2011/0250582 | A1 * | 10/2011 | Gates | C09K 8/582 |
| | | | | 435/3 |

OTHER PUBLICATIONS

Stahl, "Carbon Isotopes in Petroleum Geochemistry" in: Jager et al., Lectures in Isotope Geology, (New York, Springer-Verlag, 1979), pp. 274-282 (Year: 1979).*

Creaney, "Reaction of Organic Material to Progressive Geological Heating" in: Naeser et al., Thermal History of Sedimentary Basins : Methods and Case Histories, (New York, Springer-Verlag, 1989), pp. 37-52 (Year: 1989).*

Martin Schoell, P.D. Jenden, M.A. Beeunas, and D.D. Coleman, Isotope Analyses of Gases in Gas Field and Gas Storage Operations, SPE 26171, 1993, pp. 337-344.

* cited by examiner

DETECTION AND QUANTIFICATION OF GAS MIXTURES IN SUBTERRANEAN FORMATIONS

CROSS-REFERENCE TO RELATED APPLICATIONS

This application is a continuation-in-part of Ser. No. 13/110,646, filed May 18, 2011, which is a non-provisional application which claims the benefit of and priority to U.S. Provisional Application Ser. No. 61/352,168 filed Jun. 7, 2010, entitled "Detection and Quantification of Gas Mixtures in Subterranean Formations," each of which is hereby incorporated by reference in its entirety.

FIELD OF THE INVENTION

The present invention relates generally to methods and systems for determining relative quantities of gas mixtures in a reservoir compartment of a subterranean formation. More particularly, but not by way of limitation, embodiments of the present invention include methods and systems for quantifying contributions to gas mixtures in a reservoir compartment by way of isotopic analyses.

BACKGROUND

In producing hydrocarbons from subterranean formations, secondary recovery operations are often employed to enhance recovery of the hydrocarbons remaining in the subterranean formations. Secondary recovery operations usually refer to the second stage of hydrocarbon production, during which an external fluid such as water or gas is injected into the reservoir through injection wells located in the formation that is in fluid and pressure communication with the production wells. The purpose of secondary recovery is to maintain reservoir pressure and to displace hydrocarbons toward the producing wellbore.

The most common secondary recovery techniques are gas injection and waterflooding. Normally, gas and/or water is injected into the production zone to sweep oil from the reservoir or to otherwise provide a motive pressure to enhance recovery. Typically, the secondary recovery stage reaches its limit when the injected fluid (water or gas) is produced in considerable amounts from the production wells and the production is no longer economical. Usually, the successive use of primary recovery and secondary recovery in an oil reservoir produces about 15% to 40% of the original oil in place.

Where injected gas is used, a continuing challenge in the industry is determining whether the injected gas is reaching the producing wellbore. Additionally, it is often desired to quantitatively determine how much of the injected gas is reaching a particular producing wellbore. This information aids producers in knowing whether the injected gas is reaching its intended target and aids in determining when continuing secondary operations are becoming less economically viable.

To complicate matters, subterranean formations often contain naturally-occurring gas mixtures which confuse or further complicate determination of the amount of injected gas that is reaching the production wellbore or wellbores. The presence of naturally-occurring formation gases complicates this quantification of the injected secondary sweep gas mixtures versus the naturally-occurring gas mixtures. Compositional techniques usually fail to adequately determine the relative contributions of these gas mixtures, because the naturally-occurring gas mixtures often contain one or more of the same components as the injected gas mixtures. Even where compositional techniques can provide some estimation of the relative contributions of each gas mixture, these technique estimates are too often unacceptably inaccurate.

Conventional approaches to determining the presence of an injected gas include the use of chemical tracers. Occasionally, chemical tracers are employed to allocate production between reservoir compartments. Chemical tracers such as various radioactive isotopes, may be introduced to the reservoir by way of an injection well in communication with one or more of the reservoir compartments. By including a chemical tracer in the injected gas mixture, a producer can determine the presence of the injected gas mixture in the producing wellbore by analyzing the produced hydrocarbons for the chemical tracer. Alternatively, if desired, during drilling, samples may be extracted from the mud gas and analyzed for presence of the tracer to perform the same determination of a wellbore being drilled. One generally assumes that larger amounts of chemical tracer correspond to larger contributions of injected gas. Nevertheless, this conventional method is largely a qualitative determination and suffers from being unable to provide decent quantitative estimations of the relative amount of injected gas in the extracted hydrocarbons. Due to this method being notoriously unreliable for quantitative determinations, its use to date has been confined mostly to presence determinations and for qualitative assessments. Additionally, the tracer method is extremely expensive, making its use highly undesirable from a cost standpoint.

Occasionally, a producer is faced with a related problem of determining how much of a naturally-occurring reservoir gas mixture is reaching a wellbore versus how much of an externally-introduced reservoir gas mixture is reaching the wellbore. The externally-introduced reservoir gas may be any gas that was introduced into the reservoir from some outside source and generally refers to any gas that was not naturally-formed or found in the production reservoir. Unfortunately, the conventional methods for addressing this more general problem suffers from the same limitations as the aforementioned prior art methods.

Current methods for determining producer and injector well interactions generally consider just the time it takes for the externally introduced water or gases to reach a production well. This technique can be performed by examining neighboring production and injection wells, and their historical production and injection profiles. The historical profiles can be viewed as a chart or trend of information that can then be compared to neighboring wells to look for similar patterns of production performance related to injection. Once similar patterns are observed, a time estimate can be made, generally in months, and determination of which injection well has an influence on a neighboring production well can be made. Generally, no quantitative information exists in this technique to infer which specific intervals in the reservoir are or are not receiving water or external injection gases or pressure support. This technique may also be quite subjective and or ambiguous depending on the pattern matching capabilities of an interpreter or inconsistent nature of the paths that fluids can take within reservoir compartments that often contain unknown barriers and/or baffles to flow in different directions.

Accordingly, there is a need in the art for improved systems and methods that address one or more disadvantages of the prior art for more accurately quantitatively quantifying contributions of gas mixtures in a reservoir.

SUMMARY

The present invention relates generally to methods and systems for determining relative quantities of gases contributing to gas mixtures in a reservoir compartment of a subterranean formation. More particularly, but not by way of limitation, embodiments of the present invention include methods and systems for quantifying contributions of gas mixtures in a reservoir compartment by way of isotopic analyses.

One example of a method for determining relative contributions of a plurality of gas mixtures to a reservoir compartment of a subterranean formation comprises the steps of: (a) externally injecting a secondary gas mixture in the subterranean formation; (b) determining a first gas thermal maturity ($R_{o\_A}$) of a first gas mixture, wherein the first gas mixture contributes to a commingled gas mixture in the reservoir compartment; (c) determining a second gas thermal maturity ($R_{o\_B}$) of a second gas mixture, wherein the second gas mixture contributes to a commingled gas mixture in the reservoir compartment; (d) obtaining a plurality of samples of the commingled gas mixture at a plurality of depths, the commingled gas mixture at each depth characterized by a plurality of components, wherein the plurality of components comprises a plurality of carbon-based components, wherein each carbon-based component comprises a plurality of stable carbon isotopes; (e) analyzing each of the samples from each depth to determine a stable carbon isotope value ($\delta^{13}C$) for two or more of the carbon-based components of each sample; (f) determine a $\delta^{13}C$ ratio of the stable carbon isotope value ($\delta^{13}C$) of a first carbon-based component to the stable carbon isotope value ($\delta^{13}C$) of a second carbon-based component, wherein the first carbon-based component is one of the two or more of the carbon-based components, and wherein the second carbon-based component is another of the two or more of the carbon-based components, wherein the $\delta^{13}C$ ratio is determined at each of the plurality of depths; (g) determining a commingled gas mixture thermal maturity ($R_{o\_m}$) corresponding to the $\delta^{13}C$ ratio determined in step (ff), wherein determining the commingled gas mixture thermal maturity ($R_{o\_m}$) is determined according to a known relationship of thermal maturity as a function of $\delta^{13}C$ ratio; and (h) determining the relative contribution of the second gas mixture to the reservoir compartment by evaluating the quantity ($R_{o\_m}-R_{o\_A}$)/($R_{o\_B}-R_{o\_A}$) or mathematical equivalent thereof to produce a second gas contribution (y) or determining the relative contribution of the second gas mixture to the commingled gas mixture using the determined $R_{o\_m}$, $R_{o\_A}$, and $R_{o\_B}$.

One example of a method for determining relative contributions of a plurality of gas mixtures to a reservoir compartment of a subterranean formation comprises the steps of: (a) determining a first gas thermal maturity ($R_{o\_A}$) of a first gas mixture, wherein the first gas mixture contributes to a commingled gas mixture in the reservoir compartment; (b) determining a second gas thermal maturity ($R_{o\_B}$) of a second gas mixture, wherein the second gas mixture contributes to a commingled gas mixture in the reservoir compartment; (c) obtaining a plurality of samples of the commingled gas mixture at a plurality of depths, the commingled gas mixture at each depth characterized by a plurality of components, wherein the plurality of components comprises a plurality of carbon-based components, wherein each carbon-based component comprises a plurality of stable carbon isotopes; (d) analyzing each of the samples to determine a stable carbon isotope value ($\delta^{13}C$) of one of the carbon-based components of each sample; (e) determining a commingled gas mixture thermal maturity ($R_{o\_m}$) corresponding to the stable carbon isotope value ($\delta^{13}C$) determined in step (d) wherein determining the commingled gas mixture thermal maturity ($R_{o\_m}$) is determined according to a known relationship of thermal maturity as a function of stable carbon isotope values for the carbon-based component; and (f) determining the relative contribution of the second gas mixture to the reservoir compartment by evaluating the quantity ($R_{o\_m}-R_{o\_A}$)/($R_{o\_B}-R_{o\_A}$) or mathematical equivalent thereof to produce a second gas contribution (y).

Where a commingled gas mixture is characterized by a plurality of components, wherein the plurality of components comprises a plurality of carbon-based components, wherein each carbon-based component comprises a plurality of stable carbon isotopes, one example of a method for determining relative contributions of a plurality of gas mixtures to the commingled gas mixture in a reservoir compartment of a subterranean formation comprises the steps of: (a) receiving a first gas thermal maturity ($R_{o\_A}$) of a first gas mixture, wherein the first gas mixture contributes to a commingled gas mixture in the reservoir compartment; (b) receiving a second gas thermal maturity ($R_{o\_B}$) of a second gas mixture, wherein the second gas mixture contributes to a commingled gas mixture in the reservoir compartment; (c) receiving a stable carbon isotope value ($\delta^{13}C$) for two or more of the carbon-based components at each of the wellbore depths; (d) determine a $\delta^{13}C$ ratio of the stable carbon isotope value ($\delta^{13}C$) of a first carbon-based component to the stable carbon isotope value ($\delta^{13}C$) of a second carbon-based component, wherein the first carbon-based component is one of the two or more of the carbon-based components, and wherein the second carbon-based component is another of the two or more of the carbon-based components, wherein the $\delta^{13}C$ ratio is determined at each of the plurality of depths; (f) determining a commingled gas mixture thermal maturity ($R_{o\_m}$) corresponding to the $\delta^{13}C$ ratio determined in step (d), wherein determining the commingled gas mixture thermal maturity ($R_{o\_m}$) is determined according to a known relationship of thermal maturity as a function of $\delta^{13}C$ ratio; and (g) determining the relative contribution of the second gas mixture to the reservoir compartment by evaluating the quantity ($R_{o\_m}-R_{o\_A}$)/($R_{o\_B}-R_{o\_A}$) or mathematical equivalent thereof to produce a second gas contribution (y).

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein.

Figure 1A:
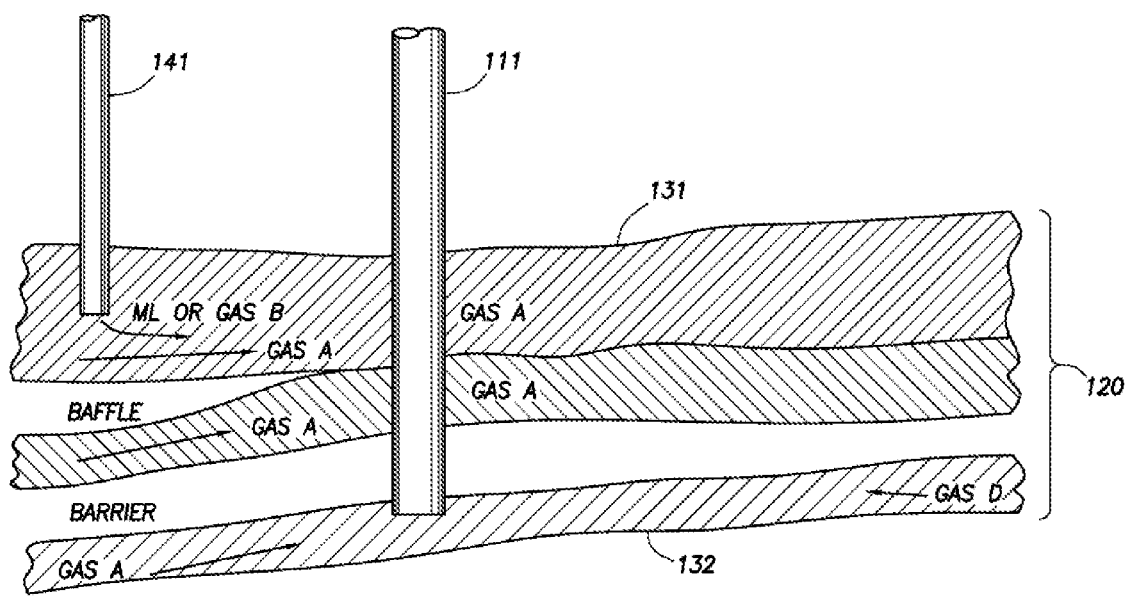
FIG. 1A illustrates a wellbore disposed in a subterranean formation intersecting a plurality of reservoirs in accordance with one embodiment of the present invention.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present invention relates generally to methods and systems for determining relative quantities of gas mixtures in a reservoir compartment of a subterranean formation. More particularly, but not by way of limitation, embodiments of the present invention include methods and systems for quantifying contributions of gas mixtures in a reservoir compartment by way of isotopic analyses.

Where more than one gas mixture contributes to the total gas mixture in a reservoir compartment, the methods and systems disclosed herein rely in part on the differing thermal maturities of the different gas mixtures to estimate the relative quantity of each gas mixture present in the total gas mixture. This method may be carried out at each depth to determine relative contributions of each gas mixture to the total gas mixture along the depth or length of a wellbore. The thermal maturities of each gas may be estimated by lab analysis and/or by reference to stable carbon isotopic analysis as described further below.

In certain embodiments, the two gas mixtures of interest possess differing thermal maturities, due to the nature of the formation of each gas mixture under different geologic conditions. In this type of example, the methods and systems disclosed herein are capable of determining the relative contribution of each mixture to a commingled wellbore stream.

Advantages of certain embodiments of the present invention include, but are not limited to, higher accuracies and ease of application as compared to conventional methods.

Reference will now be made in detail to embodiments of the invention, one or more examples of which are illustrated in the accompanying drawings. Each example is provided by way of explanation of the invention, not as a limitation of the invention. It will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations that come within the scope of the invention.

FIG. 1A illustrates a wellbore disposed in a subterranean formation intersecting a plurality of reservoirs in accordance with one embodiment of the present invention. Here, hydrocarbon producing wellbore 111 is disposed in subterranean formation 120. Wellbore 110 intersects two hydrocarbon-bearing reservoir compartments 131 and 132. Injection wellbore 141 is provided for injecting Gas B, which in certain embodiments may be a miscible injectant gas. Each reservoir compartment 131 and 132 possesses commingled gas mixtures that result from contributions of other gases. In reservoir compartment 131, for example, the commingled gas mixture reaching the wellbore at various depths results from the commingling of Gas A and Gas B.

In reservoir compartment 132, on the other hand, the commingled gas mixture reaching producing wellbore 111 results from the commingling of Gas A and Gas C. Thus, due to reservoir connectivity and geology, gas mixtures reaching producing wellbore 111 will necessarily have different compositions resulting from different contributions of gas from other sources.

Figure 1B:
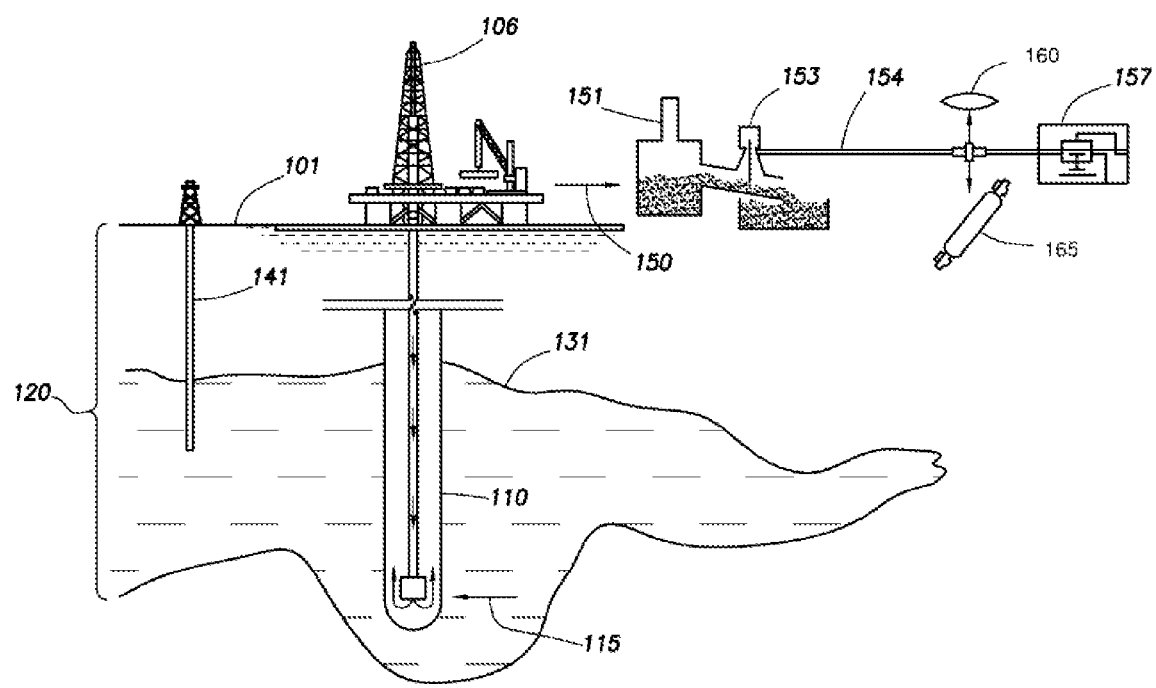
FIG. 1B illustrates a wellbore disposed in a subterranean formation intersecting a reservoir in accordance with one embodiment of the present invention.

FIG. 1B illustrates a wellbore disposed in a subterranean formation intersecting a reservoir in accordance with one embodiment of the present invention. In particular, wellbore 110 is disposed in subterranean formation 120 and intersects reservoir compartment 131.

Reservoir compartment 131 may be charged with multiple gas mixtures from different sources to form a commingled gas mixture. In some cases, a gas mixture might naturally-form in reservoir compartment 131. In other cases, gas mixtures may be introduced from another source external to reservoir compartment 131. While many combinations and permutations of this sort are possible, for illustrative purposes, this example discusses a first gas mixture in reservoir compartment 131 that originated from a first source (not shown) external to reservoir compartment 131. Here, a second gas mixture also contributes to the commingled gas mixture present in reservoir compartment 131.

The second gas mixture may be any externally-introduced gas that is present in reservoir compartment 131 due to being introduced from some source external to reservoir compartment 131. In some cases, the second gas mixture may be an injected gas that is introduced into reservoir compartment 131 for the purpose of one or more secondary recovery operations. In certain embodiments, the second gas mixture may be a gas mixture that was introduced into reservoir compartment 131 by way of some other reservoir compartment (not shown) by natural or man-made mechanisms. In this example, a second gas mixture such as a miscible injectant gas is introduced via injection well 141 to sweep hydrocarbons towards producing wellbore 110. In some cases, the second gas mixture is preferably a miscible gas used to enhance recovery of hydrocarbons by way of a secondary recovery operation.

The quantification methods disclosed herein rely in part on the differing thermal maturities of the first gas mixture as compared to the second gas mixture. The differing thermal maturities of each gas mixture are due to geochemical differences between the gas mixtures owing to either (i) different source rock facies which generated the petroleum fluids that charged the different compartments, or (ii) similar source rock facies that charged the compartments at different stages of its thermal history, or (iii) a combination of these two geologic processes. Similarly, intra-reservoir alterations processes such as biodegradation, water washing, oil to gas cracking and other post-petroleum charge geologic processes may also affect chemical variation in the gas mixtures. Because the gas mixtures were subject to different geological conditions during their geologic evolution, the components of each gas mixture contain different distributions of carbon isotopes. That is, the first gas mixture may have hydrocarbon components containing more stable $^{13}C$ carbon isotope as compared to $^{12}C$ carbon isotope than the second gas mixture. Stable carbon isotope values referred to here are relative to the PeeDee Belemnite standard (PDB) and represented by $$\delta^{13}C = \left(\frac{\frac{^{13}C}{^{12}C}\text{sample}}{\frac{^{13}C}{^{12}C}\text{standard}} - 1\right) \cdot 1000.$$

As will be described further below, these differences in carbon isotope values allow estimation of the respective thermal maturities of each gas mixture of interest (e.g. the first gas mixture, the second gas mixture, and the commingled gas mixture). Additionally, as will be described further below, $\delta^{13}C$ ratios of carbon isotope values of two carbon-based components may also be used to estimate the respective thermal maturities of each gas mixture. Knowing the thermal maturity of each of the gas mixtures then allows for quantitative estimation of the relative contributions of the first and second gas mixtures that produced the commingled wellbore gas mixture. These determinations may be carried out at a plurality of depths so as to estimate the relative contribution of each gas mixture as a function of wellbore depth. The term "depth," as used herein, refers to any longitudinal length extending along a wellbore, and is not limited to vertical depths. In this way, the term, "depth," equally applies to longitudinal wellbore lengths whether the well is vertical, deviated, or horizontal.

Because the methods herein rely in part on differing thermal maturities of the first gas mixture as compared to the thermal maturity of the second gas mixture, the methods herein realize optimum efficacy when the first gas mixture and the second gas mixtures possess differing thermal maturities. In certain embodiments, the methods herein are capable of effectively determining relative contributions of each gas mixture to the commingled gas mixture with acceptable errors even when the thermal maturities differ from one another by no more than about 3 percent. Additionally, as will be apparent to a person of ordinary skill in the art with the benefit of this disclosure, the methods herein are extremely easy to implement in the field and are susceptible to being incorporated in automated devices at the wellbore site for providing logs of relative contributions of each gas as a function of wellbore depth.

Figure 2:
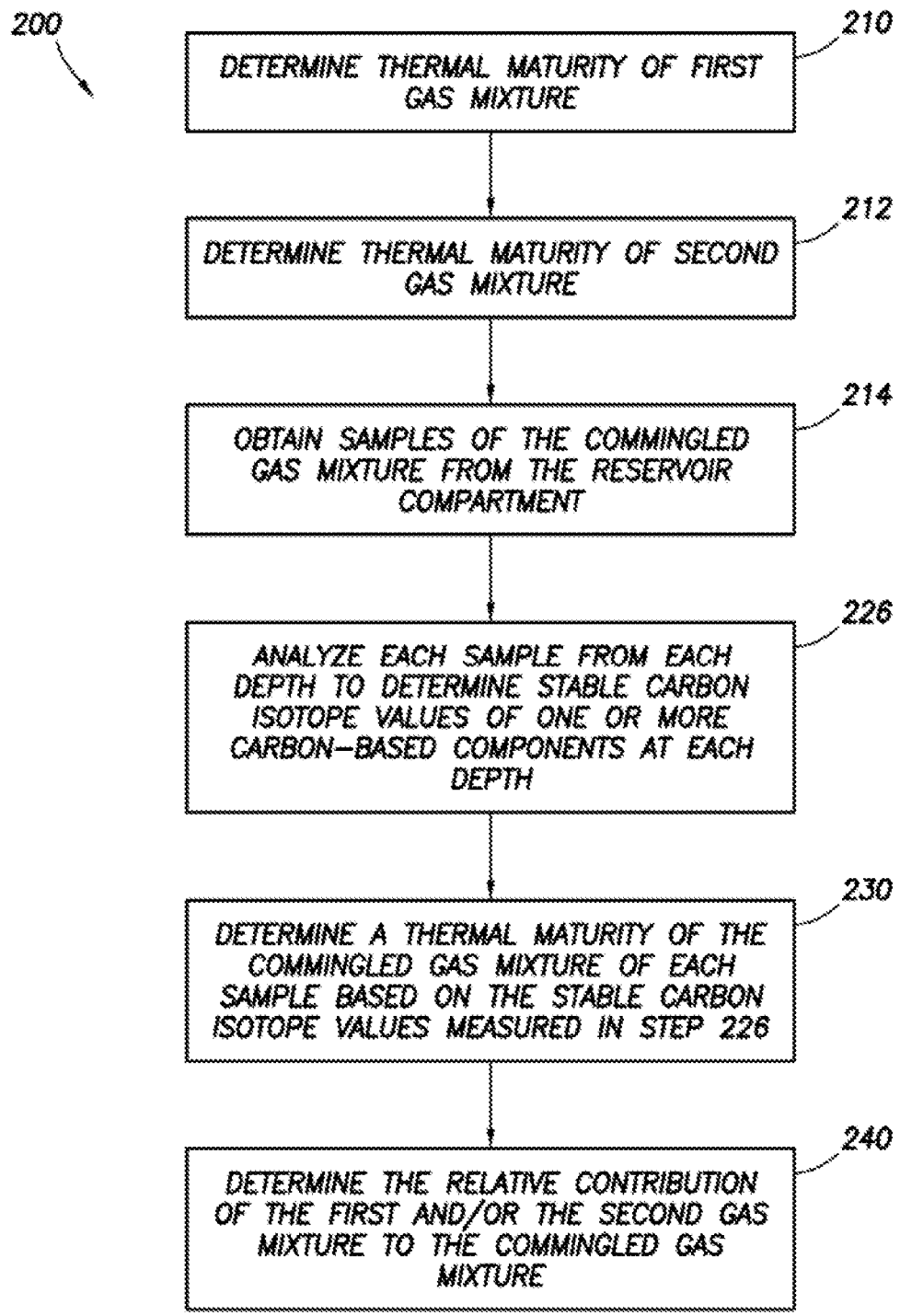
FIG. 2 illustrates a flow chart for a method for quantifying contributions of gas mixtures in a reservoir compartment in accordance with one embodiment of the present invention.

FIG. 2 illustrates a flow chart for method 200 for quantifying contributions of gas mixtures to a reservoir compartment in accordance with one embodiment of the present invention. Method 200 is explained with reference to the system shown in FIG. 1. As described above, a first gas mixture (not shown) and a second gas mixture (not shown) each contribute to charging reservoir compartment 131 to form commingled gas mixture 115.

Method 200 realizes optimal efficacy when the thermal maturity of the first gas mixture differs from the thermal maturity of the second gas mixture by some threshold tolerance level. In certain embodiments, the threshold tolerance level is at least about 2%, at least about 3%, or at least about 5%.

In step 210, the thermal maturity ($R_{o\_A}$) of the first gas mixture is determined, and in step 212, the thermal maturity ($R_{o\_B}$) of the second gas mixture is determined. This thermal maturity determination may be by way of lab analysis or other method known in the art for determining thermal maturity of a gas mixture. In certain embodiments, one or more stable carbon isotope values are measured and then, a thermal maturity is determined by reference to a known relationship between the stable carbon isotope value(s) and thermal maturity. In certain embodiments, this known relationship is a linear relationship.

In step 226, samples of commingled gas mixture 115 are obtained at a plurality of wellbore depths. In certain embodiments, the gas samples are obtained at various wellbore depth intervals as the wellbore is being drilled. As drilling rig 106 extends wellbore 110 to greater depths, samples may be obtained at a plurality of depths along the length of wellbore 110. In certain embodiments, mixture samples may be obtained from returning rock cuttings and drilling mud 150, which degases from mud receiving tank 151 by way of degassing tank 153. In some cases, mud gas 154 from the return drill fluid is sampled as substantially representative of the commingled gas mixture present at each wellbore depth being sampled. Sampling may be by way of a sampling apparatus 160 or by an on-site analyzer 157. Sampling may be desired at frequencies sufficient to minimize sample-to-sample variability to ensure a high enough resolution of measurement (e.g. to less than about 3 percent in certain embodiments). Depending on the reservoir architecture, sufficient sampling frequencies may vary from regular intervals of about every 5 feet, about every 10 feet, to about every 50 feet. Whichever sampling frequency is selected for a given portion of the wellbore, the wellbore sampling frequency selected should be sufficiently high to reflect any changes in reservoir architecture.

Each of the samples thus obtained are analyzed by way of isotopic analyzer 157 in step 226 to obtain stable carbon isotope values ($\delta^{13}C$) for one or more carbon-based components that make up commingled gas mixture 115. Alternatively, sample devices 165 may be separately analyzed in an on-site or off-site laboratory as desired. Each of the stable carbon isotope values obtained at each wellbore depth is indicative of the thermal maturity of commingled gas mixture 115 at each respective wellbore depth. Generally, the higher stable carbon isotope values are indicative of hydrocarbons having higher thermal maturities.

Thermal maturities are known to correlate well with stable carbon isotope values for each carbon-based component (e.g. with methane, ethane, propane, iso-butane, n-butane, etc.) that are found in gas mixtures. Accordingly, thermal maturities may be estimated for a given gas mixture based on a stable carbon isotope value ($\delta^{13}C$) for a particular carbon-based component (e.g. ethane) by reference to the known relationship between thermal maturity and stable carbon isotopes values. Suitable examples of known relationships of thermal maturity as a function of stable carbon isotopes values are shown in Berner and Faber, *Maturity related mixing model for methane, ethane, and propane, based on carbon isotopes*, Advances in Organic Geochemistry (1987). Known relationships for other carbon-based components may be determined as desired for use in conjunction with the methods disclosed herein.

Once the thermal maturities of the first gas mixture, the second gas mixture, and commingled gas mixture 115 are known, the relative contribution of the second gas mixture to commingled gas mixture 115 may be determined as provided in step 240. Similarly, the relative contribution of the first gas mixture to commingled gas mixture 115 may be determined as well.

Indeed, for the system illustrated in FIG. 1, where a first gas mixture and a second gas mixture that contribute to charging commingled gas mixture 115, the relative contribution of the first and second gas mixtures are characterized by the following system of equations:

$$(x)(R_{o\_A}) + (y)(R_{o\_B}) = R_{o\_m} \quad \text{[Equation 1]}$$

$$x + y = 1 \quad \text{[Equation 2]}$$

wherein x is the relative contribution of the first gas mixture,
wherein y is the relative contribution of the second gas mixture,
wherein $R_{o\_A}$ is the thermal maturity of the first gas mixture,
wherein $R_{o\_B}$ is the thermal maturity of the second gas mixture, and
wherein $R_{o\_m}$ is the thermal maturity of the mixed reservoir gases.

The relative contribution of each gas mixture may be determined by simultaneously solving this system of equations. Obviously, the above system of equations may be any mathematically equivalent operation that yields substantially the same result, including but not limited to solving the equations algebraically. Other numerical techniques may be employed to solve for the unknowns x and y as well as desired. The term, "mathematical equivalent thereof," as used herein, refers to any mathematical operation that solves for the relative contributions of the gas mixtures to a commingled gas mixture based on the equations described herein. Where algebraic substitution is employed, the relative contribution of the second gas mixture is given by the relationship, $(R_{o\_m} - R_{o\_A})/(R_{o\_B} - R_{o\_A})$. The relative contribution of the first gas mixture may then be ascertained by reference to $x = 1 - y$, since the sum of the fraction contributions of each gas mixture sum to unity.

The method thus described may also be extended to any number of gas mixtures where each gas mixture contributes to a commingled gas mixture, provided enough stable carbon isotope values are measured for enough of the components to solve for the number of unknowns inherent in the system of interest.

Figure 3:
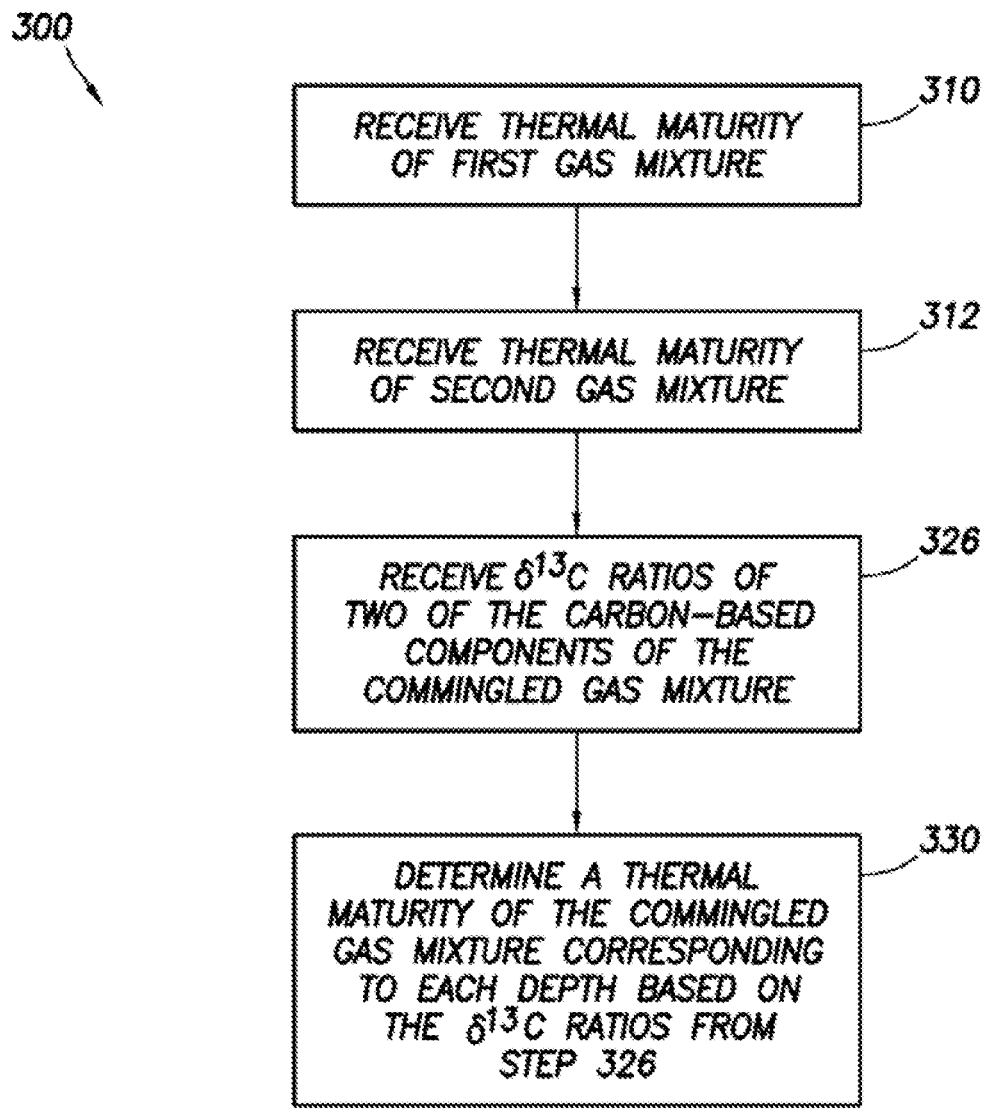
FIG. 3 illustrates an alternative embodiment of method 300 for quantifying contributions of gas mixtures to a reservoir compartment in accordance with one embodiment of the present invention.

FIG. 3 illustrates an alternative embodiment of method 300 for quantifying contributions of gas mixtures to a reservoir compartment in accordance with one embodiment of the present invention. For illustrative purposes, method 300 is explained with reference to FIG. 1.

In contrast to method 200, method 300 contemplates receiving gas thermal maturities from another entity that has independently ascertained the gas thermal maturities, as opposed to sampling and analyzing commingled gas mixture 115. Accordingly, in step 310 a thermal maturity ($R_{o\_A}$) of a first gas mixture is received, and in step 312, a thermal maturity ($R_{o\_B}$) of a second gas mixture is received.

In step 326, stable carbon isotope values ($\delta^{13}C$) are obtained for two or more carbon-based components corresponding to each wellbore depth. For example, a stable carbon isotope value ($\delta^{13}C$) of methane and a stable carbon isotope value ($\delta^{13}C$) of ethane may be obtained corresponding to each wellbore depth. Indeed, any pair of carbon-based components may be obtained in this fashion, such as, for example, methane/ethane, methane/propane, methane/n-butane, ethane/propane, ethane/n-butane, propane/n-butane, methane/iso-butane, and so forth. For the selected pair of carbon-based components selected, a $\delta^{13}C$ ratio is determined by evaluating a ratio of the stable carbon isotope value ($\delta^{13}C$) of the first carbon-based component to the stable carbon isotope value ($\delta^{13}C$) of the second carbon-based component. In this way, a $\delta^{13}C$ ratio of the $\delta^{13}C$ value of a first component to $\delta^{13}C$ of a second component is obtained corresponding to each wellbore depth.

Each of the $\delta^{13}C$ ratios thus obtained may be used to estimate a thermal maturity of commingled gas mixture 115 at each wellbore depth as provided in step 330. In step 330, the thermal maturity ($R_{o\_m}$) of commingled gas mixture 115 is determined according to a known relationship between the commingled gas mixture thermal maturity ($R_{o\_m}$) and the $\delta^{13}C$ ratios.

Figure 4:
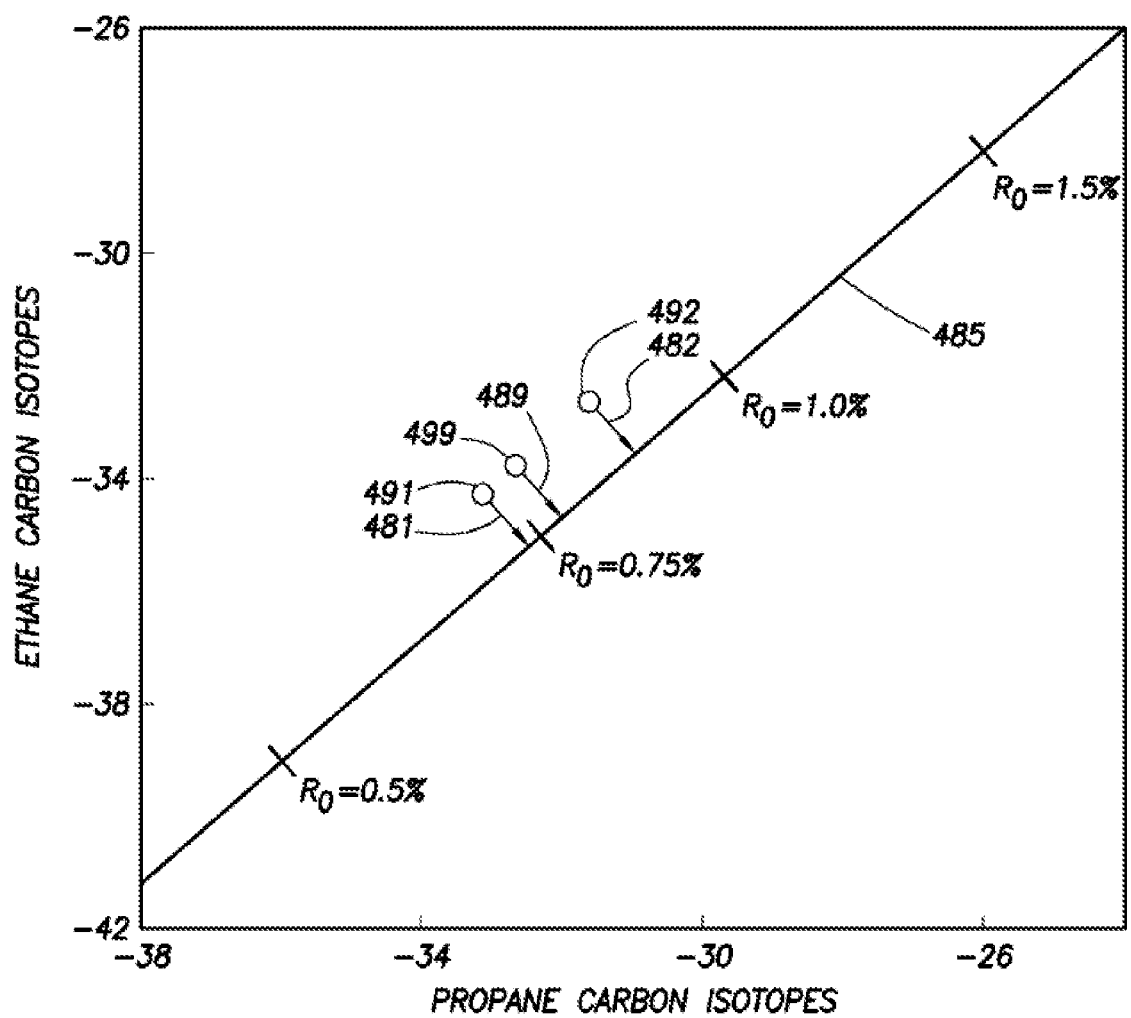
FIG. 4 shows a plot of a thermal maturity trend line against a graph of stable carbon isotope values ($\delta^{13}C$) of ethane versus stable carbon isotope values ($\delta^{13}C$) of propane.

To illustrate one example of this technique for relating thermal maturity of a gas mixture to a $\delta^{13}C$ ratio of a pair of carbon-based components, reference is made to FIG. 4. FIG. 4 shows a plot of a thermal maturity trend line against a graph of stable carbon isotope values ($\delta^{13}C$) of ethane versus stable carbon isotope values ($\delta^{13}C$) of propane. An increase in $R_o$ represents an increase in thermal maturity of the gas source. As evidenced by this plot, thermal maturity increases with increasing $\delta^{13}C$ ratio. Here, $\delta^{13}C$ ethane/propane ratios at a particular wellbore depth may be indicated on the same plot.

As one example, on FIG. 4, a $\delta^{13}C$ ethane/propane ratio of a first gas mixture is plotted as point 491, a $\delta^{13}C$ ethane/propane ratio of a second gas mixture is plotted as point 492, and a $\delta^{13}C$ ethane/propane ratio of commingled gas mixture is plotted as point 499, each of these $\delta^{13}C$ ratios being evaluated at a particular wellbore depth. The thermal maturities corresponding to each of these points 491, 492, and 499 may be determined by projecting a line normal to thermal maturity trend line 485 and ascertaining the corresponding thermal maturity at the intersection of each normal line 481, 482, and 489 and trend line 485. In this way, a thermal maturity of each gas mixture is obtained.

Other equivalent mathematical techniques may be employed to determine the thermal maturity from $\delta^{13}C$ ratios as desired. Each mathematical technique, however, relies on a known relationship between thermal maturity and $\delta^{13}C$ ratios.

Upon determining the thermal maturities of each gas, the contributions of each gas mixture to commingled gas mixture 115 may be determined in step 330 in any manner similar to step 240 of method 200. In this way, the methods herein allow for an integrative assessment of oil sweeping efficiency across an entire interval of interest, including newly drilled wells within the range of migration of injected miscible gas. The profile of thermal maturities within a reservoir interval can be integrated into the normal well log interpretation to discern differential sweep within the reservoir as well as identifying lateral and vertical scale of productive reservoir. This enables better recovery strategies (infill well drilling, well sidetracks, well recompletions, and well drilling pattern optimization), thus optimizing oil recovery. More generally, the methods herein allow the same analysis to be applied to any number of gas mixtures that contribute to a commingled gas mixture in a formation. In this fashion, the methods herein may reveal selective loss or thief zones of miscible gas which may indicate higher porosity/permeability bypass zones, faults, or permeability-anisotropic cap rocks or interbeds.

In certain embodiments, averages of multiple pairs of carbon-based components may be used to provide a cumulative effect on the different carbon constituents of a gas mixture. The individual carbon constituents (e.g. C1, C2, C3) give useful insight in themselves. For gas mixtures where the individual isotopes for C1, C2, or C3 or C3+ higher carbon numbers cannot be accurately measured, then the individual isotope trends can be used to estimate the mixing of a second gas by using a simplified strategy where the individual isotopes are used in mixing equations, without conversion to a calculated thermal maturity ($R_o$).

Optionally, the composition of each wellbore sample may be determined as well. Determining the composition of each wellbore sample provides an operator with significantly more information for interpreting the data determined by the methods disclosed herein, including allowing an operator to more effectively match measured isotope values to reservoir architecture.

It is explicitly recognized that any of the elements and features of each of the devices described herein are capable of use with any of the other devices described herein with no limitation. Furthermore, it is explicitly recognized that the steps of the methods herein may be performed in any order except unless explicitly stated otherwise or inherently required otherwise by the particular method.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations and equivalents are considered within the scope and spirit of the present invention.

The invention claimed is:

1. A method for determining reservoir connectivity, the method comprising the steps of:
    a) injecting a miscible injectant gas into a reservoir compartment in a reservoir to charge said reservoir compartment with said miscible injectant gas, said miscible injectant gas having a known or determined thermal maturity, said known or determined thermal maturity being at least 3% different from a thermal maturity of a naturally-occurring reservoir gas in said reservoir;
    b) collecting a plurality of mud-gas samples at a plurality of depths from drilling mud obtained during drilling of a new well in said reservoir;
    c) analyzing said plurality of mud-gas samples to determine a stable carbon isotope value for a first carbon-based component ($\delta 13C_1$ value) and for a second carbon-based component ($\delta 13C_2$ value);
    d) determining a stable carbon isotope ratio ($\delta 13C$ ratio) of the stable carbon isotope value for said first carbon-based component over the stable carbon isotope value of said second carbon-based component ($\delta 13C_1$ value/$\delta 13C_2$ value), thereby producing a $\delta 13C$ ratio corresponding to each of said plurality of depths;
    e) determining a relative contribution of said miscible injectant gas to each of said plurality of mud gas samples using equations:

$(x)(Ro\_A)+(y)(Ro\_B)=Ro\_m$ [Equation 1]

$x+y=1$ [Equation 2]

wherein x is a relative contribution of said naturally occurring reservoir gas to said mud gas sample,
    wherein y is a relative contribution of said miscible injectant gas to said mud gas sample,
    wherein Ro_A is a thermal maturity of said naturally occurring reservoir gas,
    wherein Ro_B is a thermal maturity of said miscible injectant gas,
    wherein Ro_m is a thermal maturity of said mud gas sample,
    wherein thermal maturity is determined according to a known relationship between thermal maturity and $\delta 13C$ ratio;
    thereby quantifying said miscible injectant gas at each depth and determining if said new well is thereby connected with said reservoir compartment at said depth.

2. The method of claim 1, wherein said known relationship is a linear relationship of thermal maturity to $\delta 13C$ ratio.

3. The method of claim 1, wherein said known relationship is a linear relationship of thermal maturity to $\delta 13C$ ratio, and wherein the step of determining the thermal maturity comprises:
    (a)(i) plotting the linear relationship $\delta 13C$ of the first carbon-based component versus $\delta 13C$ of the second carbon-based component to form a thermal maturity trend line on a first plot; (ii) for each $\delta 13C$ ratio in step (e), selecting the thermal maturity where the $\delta 13C$ of the first carbon-based component and the $\delta 13C$ of the second carbon-based component intersect said trend line; or
    (b) any mathematical equivalent of the combination of steps (a)(i)-(ii).

4. The method of claim 1, wherein the first carbon-based component is methane and the second carbon-based component is ethane.

5. The method of claim 1, wherein said first carbon-based component is ethane and said second carbon-based component is propane.

6. The method of claim 1, wherein said first carbon-based component is methane and said second carbon-based component is propane.

7. The method of claim 1, wherein said plurality of mud-gas samples are obtained at regular intervals of about every 50 feet of well depth.

8. The method of claim 1, wherein said plurality of mud-gas samples are obtained at regular intervals of about every 10 feet of well depth.

9. The method of claim 1, wherein said plurality of mud-gas samples are obtained at regular intervals of about every 5 feet of well depth.

10. The method of claim 1, wherein said known or determined thermal maturity is at least 5% different from said thermal maturity of a naturally-occurring reservoir gas.

* * * * *